United States Patent [19]

Alcala et al.

[11] Patent Number: 5,127,405
[45] Date of Patent: Jul. 7, 1992

[54] BIOMEDICAL FIBER OPTIC PROBE WITH FREQUENCY DOMAIN SIGNAL PROCESSING

[75] Inventors: J. Ricardo Alcala, Chatham; Beauford W. Atwater, Edison, both of N.J.

[73] Assignee: The BOC Group, Inc., New Providence, N.J.

[21] Appl. No.: 481,131

[22] Filed: Feb. 16, 1990

[51] Int. Cl.$^5$ ............................. A61B 1/06; A61B 6/00
[52] U.S. Cl. ................................... 128/633; 128/634; 128/665
[58] Field of Search ............... 128/633, 634, 665, 666, 128/667

[56] References Cited

U.S. PATENT DOCUMENTS

| | | | |
|---|---|---|---|
| 4,476,870 | 10/1984 | Peterson et al. | 128/634 |
| 4,556,057 | 12/1985 | Hiruma et al. | 128/634 |
| 4,576,173 | 3/1986 | Parker et al. | 128/633 |
| 4,579,417 | 4/1986 | Ih | 350/96.11 |
| 4,592,361 | 6/1986 | Parker et al. | 128/633 |
| 4,675,529 | 6/1987 | Kushida | 250/458.1 |
| 4,727,730 | 3/1988 | Boiarski et al. | 128/667 |
| 4,810,655 | 3/1989 | Khalil et al. | 436/138 |
| 4,947,850 | 8/1990 | Vanderkooi et al. | 128/654 |
| 4,975,581 | 12/1990 | Robinson et al. | 128/633 |
| 4,981,138 | 1/1991 | Deckelbaum et al. | 128/665 |

FOREIGN PATENT DOCUMENTS

| | | |
|---|---|---|
| 0252578 | 1/1988 | European Pat. Off. . |
| 0283289 | 9/1988 | European Pat. Off. . |
| 2132348 | 7/1984 | United Kingdom . |

OTHER PUBLICATIONS

Bright, "Remote Sensing with a Multifrequency Phase-Modulation Fluorometer", SPIE, vol. 909, pp. 23 et seq.

Bright, et al., "A new frequency-domain fluorometer for the rapid determination of picosecond rotational-correlation times", J. Applied Physics, vol. 61, pp. 8-11 (Jan. 1987).

Bright, et al., "Rapid-scanning frequency-domain fluorometer with picosecond time resolution", Applied Optics, vol. 26, No. 17, pp. 3526 et seq.

Feddersen, et al., "Digital parallel acquisition in frequency domain fluorimeter", Rev. Sci. Instrum. 60(9), vol. 60, pp. 2933-2934.

Alcala, Comment on "Digital parallel acquisition in frequency domain fluorometry", Rev. Sci. Instrum. 62(6), pp. 1672-1673.

"Yearly Review, Synthetic Models of Photosynthesis", Photochemistry and Photobiology, vol. 47, No. 6, pp. 923-929, 1988.

Jordan, et al., "Physiological pH Fiber-Optic Chemical Sensor Based on Energy Transfer", Anal. Chem., 1987, 59, 437-439.

*Primary Examiner*—William E. Kamm
*Assistant Examiner*—Kevin Pontius
*Attorney, Agent, or Firm*—Roger M. Rathbun; Larry R. Cassett

[57] ABSTRACT

A fiber optic probe incorporating a luminescent composition is used to monitor conditions within a living subject. Response light from the fiber optic is detected and a frequency domain representation of the response light is derived. Characteristics of the frequency domain representation are used to derive values for luminescence lifetimes or similar decay parameters and these values in turn are translated into values of the conditions to be sensed.

30 Claims, 4 Drawing Sheets

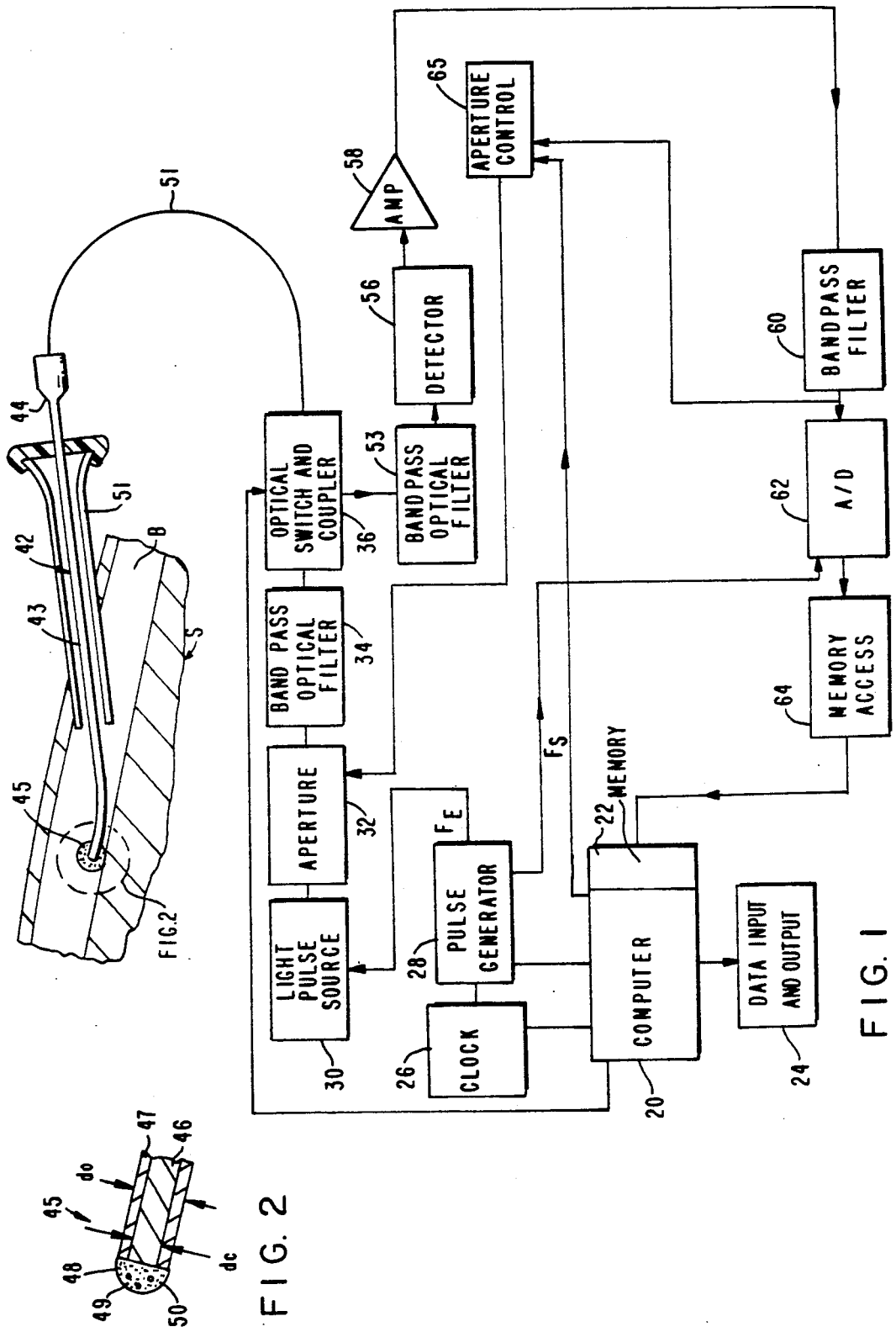

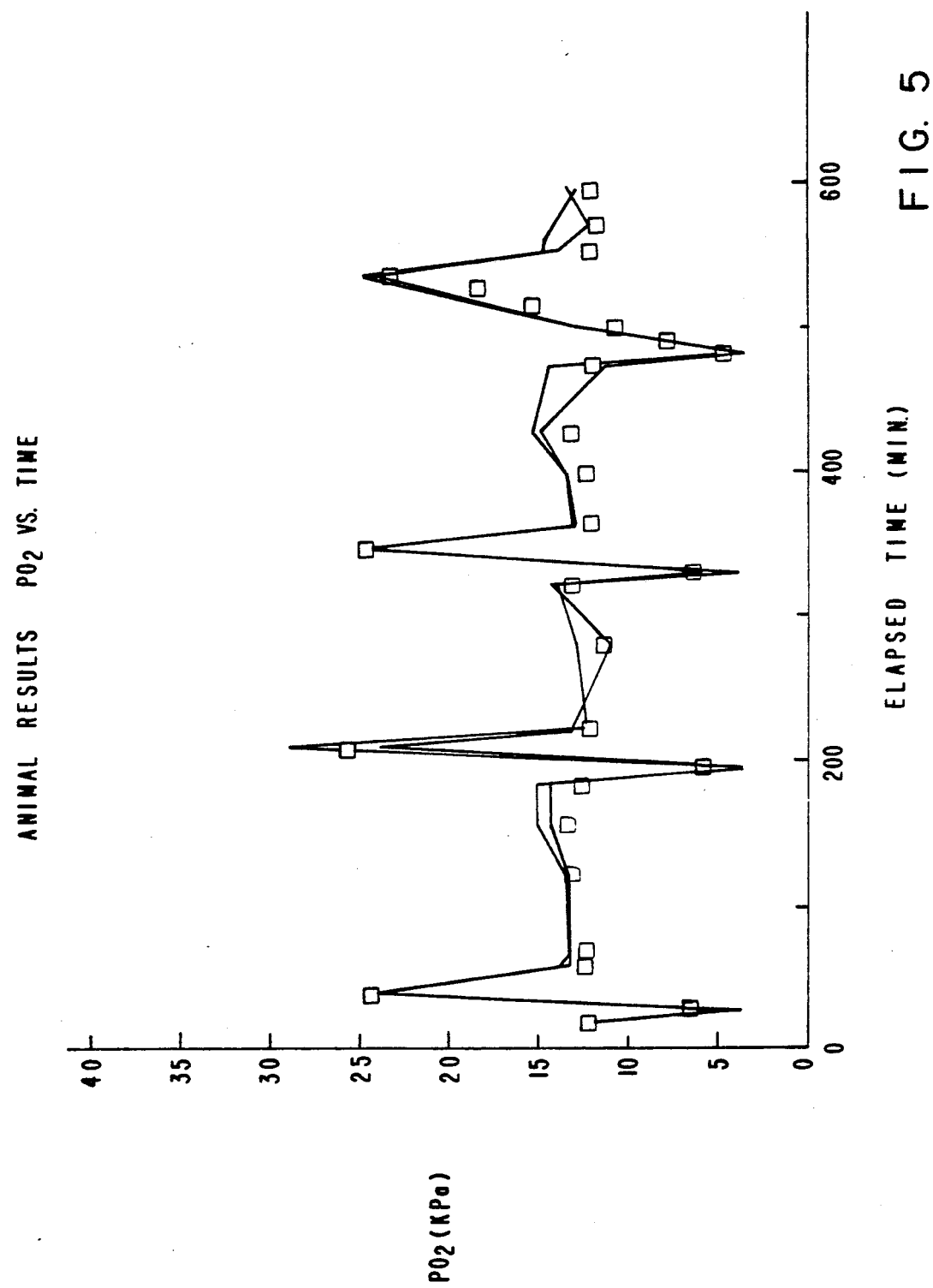

BIOMEDICAL FIBER OPTIC PROBE WITH FREQUENCY DOMAIN SIGNAL PROCESSING

BACKGROUND OF THE INVENTION

It has long been recognized that the fluorescent and phosphorescent properties of certain materials vary in accordance with properties of the surroundings. For example, certain luminescent materials are subject to "quenching" or extinction of their luminescent response by oxygen. Various instruments have been proposed to exploit such phenomena in chemical and/or physical measuring instruments. For example, U.S. Pat. No. 4,810,655 discloses an instrument for determining oxygen concentration by applying excitation light to a fluorescent material and observing the time dependence of fluorescence decay. As the oxygen concentration in the environment surrounding the luminescent material changes, the pattern of fluorescent decay with time also changes. The '655 instrument employs a "light pipe" for transmitting the requisite excitation light to the luminescent material and for transmitting the light back to a sensor. European Patent Application 0,283,289 monitors the intensity of long lived phosphorescent emissions from a phosphorescent material bonded to an end of an optical fiber. The optical fiber is small enough that it can be inserted through a small tube, such as an intravenous catheter or the like, so that the phosphorescent material lies within a blood vessel and acts as an in vivo $PO_2$ sensor. Other fiber optic based $PO_2$ sensors are disclosed in U.S. Pat. No. 4,476,870 and European Patent Application 0,252,578. U.S. Pat. No. 4,576,173 discloses an instrument for monitoring relatively long-lived "singlet oxygen emission" or phosphorescence exhibited by certain bodily tissues such as tumors when those tissues are treated with photosensitizing chemicals and exposed to incident light. This instrument employs a chopped or pulsatile incident light. In order to segregate the relatively long-lived "singlet oxygen emissions" or phosphorescence from the relatively short lived fluorescence of the sensitizing chemicals, the instrument employs a quadrature detection system. A signal in phase with the chopped excitation light is segregated from the quadrature component 90 degrees out of phase with the chopped excitation light signal. The quadrature signal, out of phase with the chopping signal, consists essentially of the desired long-lived "singlet oxygen emission" signal. Although the reference mentions "frequency domain signal processing", the signal processing involved is nothing more than isolation of the quadrature signal from the in phase signal. The amplitude of the isolated quadrature signal is monitored to monitor the desired "singlet oxygen emission" intensity.

Although these and other fiber optic based luminescence probes and instruments have been proposed for monitoring chemical and/or physical conditions within the bodies of living subjects, the instruments available heretofore have suffered from certain significant drawbacks. For ease of insertion into the body, a fiber optic probe should be less than about 450 micrometers in diameter. It is especially important to keep the diameter of each fiber optic probe to a minimum when a plurality of fiber optic probes are to be passed into the body through a single opening, as through a lumen of a single intravascular catheter or hypodermic needle. The amount of luminescent material which can be accommodated in a probe of such small diameter is limited. Moreover, the total energy which can be applied to the luminescent material by excitation light transmitted along the fiber optic is directly proportional to the cross-sectional area of the fiber optic. Thus, only limited light energy can be applied to excite the luminescent material in a fiber optic probe. All of these factors tend to limit the amplitude of the response light emitted by the luminescent material and transmitted back along the fiber to the proximal end. Even highly sensitive photodetectors will provide only a weak signal. Further, the signal is susceptible to interference from many sources, including changes in optical and/or electronic components with time. The weak response signal from the actual luminescent material at the probe may be effectively hidden by the background noise. Stated another way, such instruments have had poor signal to noise ratios. This problem has been particularly severe in the case of instruments arranged to monitor the decay rate of relatively short-lived luminescent phenomena such as fluorescence or rapidly-decaying phosphorescence.

Thus, prior to the present invention, there have been significant, unmet needs for still further improvement in luminescence based biomedical monitoring apparatus and methods.

SUMMARY OF THE INVENTION

The present invention addresses these needs.

One aspect of the present invention provides apparatus for monitoring a condition within a living subject. Apparatus according to this aspect of the invention preferably includes a probe adapted for insertion into the body of a subject, the probe including an elongated optically transmissive fiber having a proximal end and a distal end. The probe also includes a luminescent composition mounted at the distal end of the fiber in optical communication therewith, such that the luminescent composition can receive excitation light transmitted through the fiber and such that response light produced by luminescent of the composition will be sent back to the approximal end of the fiber. The luminescent composition has one or more luminescent decay time parameters affected by the condition to be monitored when the distal end of the probe is disposed within the body of the subject. For example, the luminescent composition may include a phosphorescent material which is quenched by oxygen such that its phosphorescence decays more rapidly in the presence of oxygen.

The apparatus preferably also includes means for applying excitation light to the luminescent composition through the fiber. Desirably, the excitation light applying means is arranged to apply excitation light varying cyclically in amplitude and incorporating components at a plurality of excitation frequencies. Accordingly, the luminescent composition will emit response light varying cyclically and including a plurality of response components at a plurality cf response frequencies, and this response light will be transmitted through the fiber to the proximal end thereof. The apparatus preferably also includes means for detecting the response light at the proximal end of the fiber and deriving a frequency domain representation of the response light including at least one characteristic of each of the plurality of response components. The apparatus also includes means for deriving values of one or more luminescence decay time parameters of the composition from the characteristics included in frequency domain representation. As the derived luminescence decay parameters represent the luminescence of the material under the conditions prevailing within the subject, these luminescence decay parameters will vary with the conditions within the subject.

Conversion of the detected response light into a frequency domain representation, as by Fourier or similar transforms, and determination of the decay parameters from the transformed information provides several advantages. Because the instrument monitors decay time parameters rather than luminescence intensity, it is essentially insensitive to changes in the luminescence intensity such as may be introduced by deterioration or bleaching of the luminescent material, deviations in manufacture of the probe or changes in the optical path of the instrument. Determination of decay time parameters from the frequency domain information provides markedly enhanced sensitivity to very brief decay times and very small changes in decay time. Thus the preferred instruments according to this aspect of the present invention can monitor the very brief decay times associated with fluorescence and rapidly decaying phosphorescence, and can detect the very small changes in those brief decay times occasioned by changes in environmental conditions. Accordingly, those luminescent materials which have only fluorescence or brief phosphorescence sensitive to the condition to be monitored but which have other desirable properties such as high sensitivity to the condition to be monitored can be employed in the luminescent composition of the probe. Thus, the luminiscence being monitored may have a decay time on the order of 100 nanoseconds, 10 nanoseconds or even less.

Moreover, the frequency domain transformation provides an inherent averaging or noise suppression action. Thus the characteristics of the frequency domain representation derived by the frequency domain transformation and the luminescent decay time parameters determined from the characteristics of the frequency domain representation have relatively low sensitivity to noise or random variations in the response light signal. Noise can also be suppressed by monitoring many cycles of the cyclically varying response light and averaging the results in the time domain. However, the noise suppression effect of the frequency domain transformation permits derivation of decay time characteristics having a given degree of accuracy with monitoring of a lesser number of response light cycles than would be required with only time domain averaging under equivalent conditions of signal to noise ratio in the response signal. This in turn allows measurement of the conditions prevailing within the subject in a relatively brief time, and hence permits monitoring of rapidly charging conditions. Using the frequency domain transformation approach, it is practical to monitor conditions within a living subject using a probe of a very small diameter, without substantial loss of accuracy. In preferred apparatus according to this aspect of the present invention, the fiber optic is less than about 450 micrometers in diameter, more preferably less than about 200 micrometers, and most preferably about 140 micrometers or less in diameter. The luminescent composition desirably is provided as a mass at the distal end of the fiber optic, and the diameter or dimension of the mass in the directions transverse to the direction of elongation of the fiber desirably is also less than about 450 micrometers or preferably about 200 micrometers and most preferably about 140 micrometers or less. A plurality of such small-diameter fiber optics may be employed in a composite probe including a plurality of luminescent compositions while still maintaining the overall diameter of the probe within reasonable limits.

Most preferably, the means for detecting the response light and deriving a frequency domain representation are arranged to sample the amplitude of the response light to thereby provide a response series of sample values each representing the amplitude of the response light at a predetermined point in the repetitive response light cycle. The means for deriving a frequency domain representation most desirably also includes means for transforming the response series of sample values into the frequency domain representation, as by applying a Fourier transform to the response series of sample values. Preferably, the sampling means includes means for directly sampling the response light, i.e. for sampling the response light or an electrical signal representing the response light, without any intermediate frequency shifting or cross-correlation steps prior to sampling. The apparatus according to the present invention may incorporate elements disclosed in the commonly assigned, copending U.S. Patent Application of Jose Ricardo Alcala, one of the coinventors herein, entitled "Frequency Domain Fluorometry using Coherent Sampling" filed of even date herewith. The disclosure of said copending application in its entirety is hereby incorporated by reference herein. As set forth in greater detail in the Alcala copending application, the sampling may be conducted at a sampling frequency lower than the fundamental or lowest frequency component in the response light signal, so that successive samples will be taken from different cycles of the fundamental. This permits sampling of very rapidly varying response light with sampling devices operating at reasonable sample repetition rates. This technique is referred to as wave skipping sampling. Most desirably, the response light includes components of a fundamental frequency and at harmonics of that frequency, and the wave skipping sampling is conducted at a sampling rate which is coherent with the response light fundamental component, so that after a given number of samples have been taken, the next sample falls on the same portion of a cycle as the first sample.

Further aspects of the present invention provide methods of monitoring a condition with a living subject. The methods according to this aspect of the present invention preferably include the steps of inserting a probe having any elongated optically transmissive fiber and a luminescent material at its distal end into a subject so that the proximal end of the fiber is accessible from outside the subject. The method further includes the step of applying excitation light varying cyclically in amplitude as discussed above to the luminescent material at the distal end of the fiber by passing the excitation light through the fiber, and detecting the response light emitted by the luminescent material by monitoring and transmitted to the proximal end of the fiber. The method further includes the steps of deriving a frequency domain representation of the response light including at least one characteristic of each of a plurality of response components at differing frequencies and deriving values of one or more luminescence decay parameters of the luminescent composition from these characteristics of the frequency domain representation. As discussed above in connection with the apparatus, the frequency domain transformation and derivation of the decay parameters from the characteristics of the frequency domain representation provides significant advantages such as speed and immunity from noise.

These and other objects, features and advantages of the invention will be more readily apparent with reference to the detailed description of the preferred embodiments set forth below, taken in conjunction with the companying drawings.

BRIEF DESCRIPTION OF THE DRAWINGS

FIG. 1 is a schematic, practically block form diagram of apparatus in accordance with a first embodiment of the invention.

FIG. 2 is a detailed view, on an enlarged scale, of a portion of the apparatus shown in FIG. 1.

FIG. 5 is a graph depicting results achieved in one monitoring method according to an embodiment of the invention.

DETAILED DESCRIPTION OF THE PREFERRED EMBODIMENTS

Figure 3:
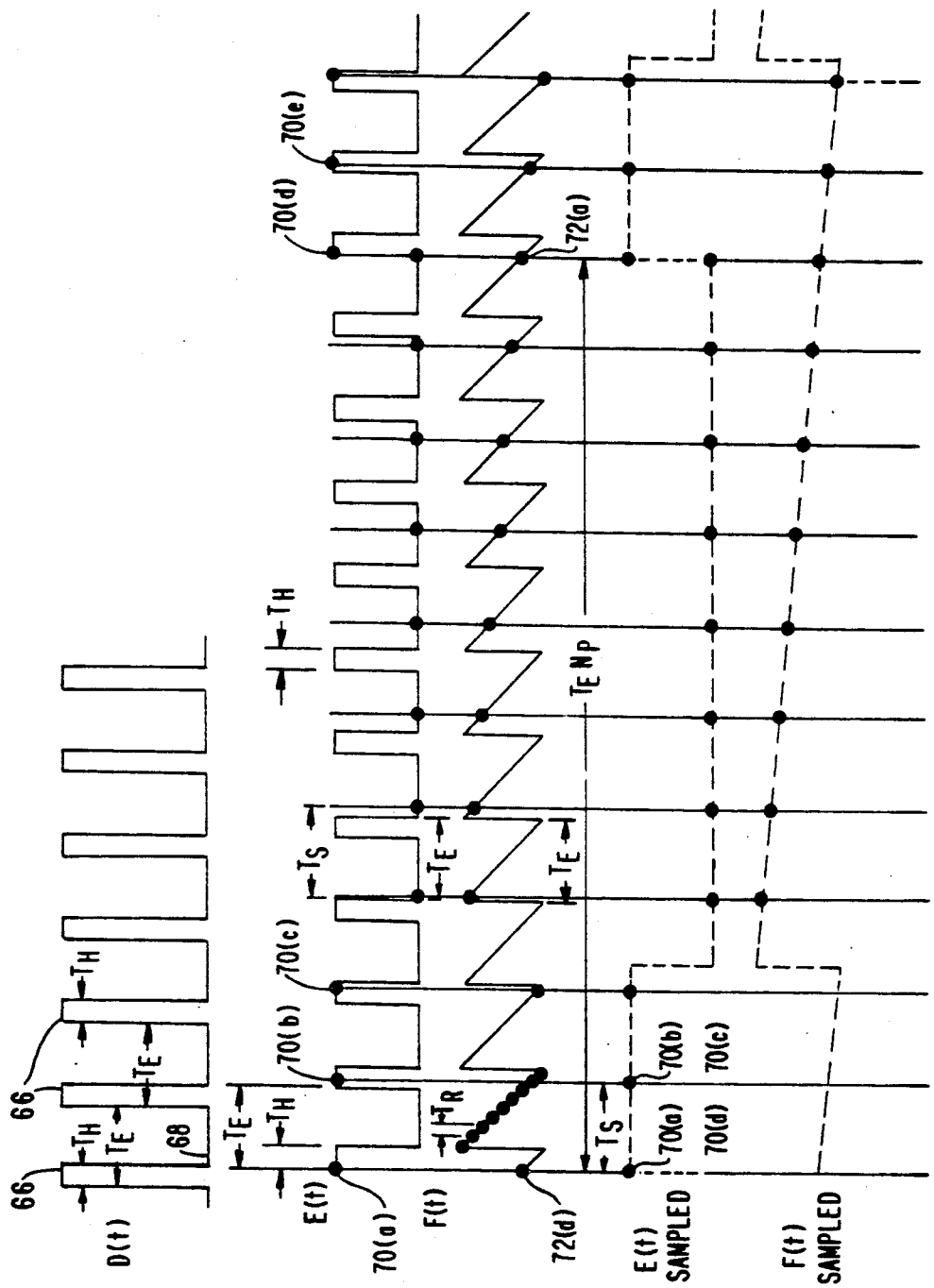
FIG. 3 is an idealized representation of certain waveforms occurring during operation of the apparatus depicted in FIG. 1.

Apparatus in accordance with one embodiment of the invention incorporates a central control computer 20 having a memory 22 and data input and output devices 24. The apparatus further includes a programmable crystal clock 26 arranged to provide clock pulses at a predetermined frequency. A programmable pulse generator 28 is arranged to provide electrical rectangular wave pulses at an excitation frequency $F_e$ and at a sampling frequency $F_s$ determined by counting clock signals from clock 26. The pulse generator 28 is arranged so that the frequencies $F_e$ and $F_s$ of the rectangular wave pulses can be selected by computer 20, as by adjusting the number of clock signals from clock 26 to be counted off by pulse generator 28 during each cycle. Further, the pulse generator is arranged to vary the breadth or duty cycle of the rectangular wave pulses provided at frequencies $F_e$ and $F_s$ as directed by computer 20.

The output of pulse generator 28 at excitation frequency $F_e$ is linked to the input connection of the light pulse source 30. The light pulse source includes an electrically controllable light emitting structure. This structure may be a device such as a light emitting diode or a combination of elements such as a continuous wave laser coupled to an acoustic-optic modulator or other device arranged to control passage of light responsive to applied electrical signals. The light output of pulse source 30 is connected through a controllable variable aperture 32 and a bandpass optical filter 34 to the input of a conventional optical switching and coupling apparatus 36. Filter 34 is arranged to permit passage of light within a predetermined wavelength band but to block light at wavelengths outside of such band. One output of switch and coupler 36 is connected to a probe 42.

Probe 42 includes an elongated optically transmissive fiber 43 having a proximal end 44 and a distal end 45. Fiber 43 is a graded index quartz optical fiber. It includes a core 46 and a cladding 47 surrounding the core along the entire length of the fiber. Both the core and the cladding are formed from transparent materials such as quartz, but the cladding has a slightly lower refractive index than the core. The fiber 43 is generally circular in a cross section. Its outside diameter $d_o$ is less than about 450 micrometers preferably less than about 200 micrometers and most preferably less than about 140 micrometers. Its core diameter $d_c$ is about 60–80% of the outside diameter, viz, about 100 micrometers where the outside diameter is about 140 micrometers and preferably less than about 100 microns.

A mass 48 of a luminescent composition comprising crystals of a phosphorescent material 49 embedded in an oxygen-permeable transparent plastic resin 50 is mounted at the distal end 45 of the fiber. Desirably, mass 48 is bonded to the fiber by adhesion of the plastic resin 50 to the material of the fiber. The diameter of mass 48 (its dimension in the direction transverse to the direction of elongation of fiber 43) is substantially the same or only slightly larger than the outside diameter $d_o$ of fiber 43. The oxygen permeable plastic resin may be a polyurethane such as Pellethane sold by Dow Chemical or a silicone polycarbonate resin such as that sold by General Electric Corporation. The phosphorescent material has a substantial sensitivity to oxygen, and desirably a substantial quenching of phosphorescence in the presence of oxygen. Among the materials which may be employed are the metallo derivatives of compounds selected from the group consisting of porphyrin; chlorin; bacteriochlorin; porphyrinogen; and the alkyl or aryl substituted derivatives of these compounds. All of the compounds have characteristic multi-ring structures with plural nitrogen atoms juxtaposed with one another adjacent the center of the structure. In the metallo derivatives, a metal atom or ion is disposed adjacent the center of the structure and is commonly considered as being bound to the nitrogen atoms of the multi-ring structure. Among the metallo derivatives which may be employed are those bearing metals selected from the group consisting of platinum and palladium. Combinations of these metals may also be used. A particularly preferred oxygen-sensitive luminescent material is platinum tetraphenyl porphyrin, commonly referred to as "platinum porphyrin".

The luminescent composition in mass 48 is in light transmitting relation with fiber 43. Thus, if light is passed along fiber 43 from its proximal end 44 to its distal end 45, at least some of that light will enter mass 48. Conversely, if light is emitted by mass 48, as by phosphorescence of the material 49, at least some of that emitted light will pass into the core 46 of fiber 43 and will pass back along the fiber, towards the proximal end 44.

The proximal end 44 of fiber 43 is connected to the optical switching and coupling apparatus 36 via conventional fiber optic interconnecting devices, schematically indicated at 51. The optical switch and coupler 36 has an output connected via a bandpass optical filter 53 to a detector 56. Detector 56 is arranged to convert light into electrical signals such that the amplitude of the electrical signals is directly related to the amplitude of the incoming light supplied to the detector. Desirably, the detector is a sensitive device having a very fast response time. Suitable detectors include photomultiplier tubes such as those supplied under the designation R928 by Hamamatsu Photonics K.K., Hamamatsu, Japan; and include avalanche photodiodes and microchannel plates, also available from the same supplier. The electrical output of detector 56 is connected to an amplifier 58. The output of amplifier 58 is connected to an electrical bandpass filter 60. Bandpass filter 60 desirably has a passband extending from slightly below fundamental excitation frequency $F_e$ to an upper frequency $F_u$ selected as discussed further below. $F_u$ typically is about 5 times to about 100 times $F_e$ and preferably about 5 to about 50 times $F_e$. Thus, the passband of filter 60 typically is arranged to encompass fundamental excitation frequency $F_e$ and a predetermined set of harmonics of that frequency such as the fundamental and the first five harmonics, the fundamental and the first 100 harmonics or the like. The output of bandpass filter 60 is connected to the signal input of a triggerable analog to digital or "A/D" converter 62. Converter 62 is arranged to capture the instantaneous amplitude of the electrical signal passed through the filter 60 upon receipt of a triggering signal, and to deliver the captured value in digital form. Output of converter 62 is connected through a direct memory access device 64 to the memory 22 of the computer 20, so that digital values supplied by converter 64 can be written into predetermined locations in memory 22 essentially instantaneously without interrupting operation of the processor in computer 20. The trigger input of converter 62 is connected to an output of pulse generator 28 carrying pulses at sampling frequency $F_s$, so that each such pulse will trigger converter 62 to capture a further sample.

The electrical output from bandpass filter 60 is also connected to a feedback aperture control circuit 65. Control circuit 65 is linked to computer 20 so that control circuit 65 can receive a target or set point value for the amplitude of the electrical signal from filter 60. Aperture control 65 is also linked to aperture 32, and aperture 32 is responsive to control signals from circuit 65. Thus, the aperture control circuit is arranged to adjust aperture 32 so as to maintain the peak amplitude of the signal from filter 60 at the selected set point. Aperture control circuit 65 is also arranged such that it will only adjust the aperture 32 upon appropriate command from computer 20 and, in the absence of such command, aperture control 65 will maintain the setting of aperture 32 at a constant value.

In a method according to one embodiment of the invention, the probe 42 is inserted into a living subject so that the distal end of the probe is disposed within the subject and hence exposed to conditions prevailing within the subject. As shown in FIG. 1, the distal end 45 of optical fiber 43 may be inserted into the blood vessel B of a living subject S, such as a human or other mammal via a conventional intravascular catheter such as an intravenous or intraarterial catheter 51. Because the fiber 43 and the mass 48 the luminescent composition at the distal end of the fiber are of relatively small diameter, such insertion may be performed readily. For example, catheter 51 may be a conventional 22 gauge catheter having an interior diameter of about 450 micrometers, and the fiber 43 may be threaded readily through such a catheter. The ability to use such a small catheter for insertion of the probe affords significant advantages in that such a small catheter is itself relatively easy to position within the blood vessel and causes only minimal trauma to the subject. The probe is positioned so that the distal end 45 lies within the blood vessel whereas the proximal end 44 of fiber 43 lies outside of the subject and hence is readily accessible for connection for through fiber optic coupling 51 to switch and coupler 36. With the probe in position, the oxygen permeable plastic resin 50 in a mass 48 reaches equilibrium with the oxygen content of the blood in blood vessel B, so that the phosphoresent material 49 within the mass is exposed to an oxygen concentration which varies with the oxygen concentration prevailing within the blood.

Computer 20 actuates the apparatus so as to perform a predetermined routine. The computer selects a fundamental frequency $F_e$ to be applied, based upon instructions provided to the computer via data input and output unit 24. Typically, the fundamental frequency $F_e$ used is directly selected by the operator from prior knowledge of the decay time range of the composition in mass 48. Thus, for each particular luminescent composition the fundamental frequency should fall within a preselected range. The fundamental frequency of the light pulses applied normally is selected so that the repetition time $T_e$ between succeeding pulses is longer than the decay time of the luminescent phenomena to be observed. Typically, $T_e$ is about 5 times to about 20 times the expected decay time. For the preferred phosphorescent materials discussed above, the decay time is about 20 microseconds, and hence $F_e$ should be about 700 Hz to about 10 KHz.

The computer sets clock 26 to generate clock pulses at a rate substantially higher than the fundamental frequency so selected, and actuates pulse generator 28 to provide a drive signal D(t) as series of electrical pulses at the so selected fundamental frequency $F_e$. The computer also controls pulse generator 28 to control the duty cycle of the waveform. As indicated in FIG. 2, the drive signal D(t) alternates between a high state 66 and a low state 68 on each cycle. The time $T_h$ during which the waveform is on or high is a relatively small proportion of the total cycle time $T_e$. The fraction $T_h/T_e$, the proportion of high or on time during each cycle is referred to herein as the "duty cycle" of the waveform. As will be readily appreciated from standard principles of mathematics, such a rectangular waveform includes a fundamental component at $F_e$ and harmonic components at frequencies which are multiples of $F_e$.

The computer also actuates pulse generator 28 to produce a series of triggering pulses at a sampling frequency $F_s$ and a sampling period $T_s$. As further discussed below, the sampling $T_s$ is selected such that $T_s$ differs slightly from $T_e$, or from some integral multiple of $T_e$. The preferred relationship between $T_s$ and $T_e$ is:

$$T_s = R_e N_w + T_e/N_p \qquad \text{(Formula I)}$$

where $N_w$ is a positive integer which may be 1 or greater than 1 and $N_p$ is a rational number having an absolute value greater than 1. Most preferably, $N_p$ is an integer. $N_p$ may be positive or negative.

The drive signal D(t) from pulse generator 28 is applied to light pulse source 30 and the light pulse source provides light varying in amplitude substantially in accordance with this drive signal D(t). Thus, during the high periods 66 of the excitation pulse signal, the light is on, whereas the light is off or at a lower value during the low periods 68. This excitation light passes through aperture 32, and bandpass filter 34 to switch and coupler 36. Computer 20 initially executes a reference cycle, during which it commands the switch and coupler to pass the excitation light into detector 56. Detector 56 provides an electrical signal representing this excitation light impinging on the detector. Aperture control 65 detects the peak amplitude of the signal from amplifier 58 and adjusts the aperture 32 to bring the amplitude of this signal into a specified range, within the operating range of converter 62. Once this adjustment has been accomplished, the aperture control 65 maintains aperture 32 at a constant setting. Bandpass filter 60 provides a filtered version of the electrical signal to A/D converter 62.

The electrical signal passing through bandpass filter 60 during this stage of the method is a reference signal representing the excitation light applied by light pulse source 30 through optical components 30, 34, and 36, together with any amplitude changes, phase shift or distortion introduced by these components or by detector 56, amplification circuit 58 and by filter 60 itself. This excitation signal E(t) (FIG. 3) is substantially in the form of a rectangular wave having the same frequency $F_e$ and repetition period $T_e$ as the original driving signal D(t). Analog to digital converter 62 samples the reference electrical signal passing through filter 60. The reference electrical signal provided by the detector is sampled directly, i.e., without any intermediate cross-correlation, mixing, or frequency-shifting steps. Stated another way, each component of the signal reaching the sampling devices or converter 62 includes the same frequencies as the corresponding component in the signal provided by the detector.

Upon each pulse of the trigger or sampling signal supplied by pulse generator 28, analog to digital converter 62 takes a sample by capturing the amplitude of the reference signal at the instant of the trigger pulse and provides a digital word representing that amplitude. Memory access unit 64 accepts these digital words as the same are generated by analog to digital converter 62 and stores them in order in memory 22. This series of operations continues, so that a reference or excitation series of values is stored in memory 22. Because the repetition period $T_s$ of the sampling or trigger signal applied to A/D converter 62 is slightly different than the repetition period $T_e$ of the excitation signal, each sample captured by A/D converter 62 occurs at a slightly different point in the waveform of the excitation signal E(t). In FIG. 3, the time of each sample is indicated on the E(t) waveform as a black dot. The first such sample 70(a) occurs at the beginning of an "on" or high period. The next sample 70(b) occurs slightly after the beginning of the "on" period during the next cycle of E(t). Sample 70(c) occurs at a slightly later point on the waveform and so on.

In the example depicted in FIG. 3, the sampling period $T_s$ is just slightly more than one $T_e$ of the excitation waveform E(t). That is, $N_w = 1$ in the expression $T_s = N_w T_e + T_e/N_p$. Where $N_w$ is greater than one, entire periods of E(t) without samples occur between successive samples. The difference between the time $T_s$ between successive samples and an integral multiple of the period $T_e$ of the excitation waveform is a rational fraction of $T_e$, i.e., $T_e/N_p$ with $N_p$ being a rational number. In the example shown in FIG. 3, $N_p$ is an integer having absolute value greater than one. Therefore, the $(N_p+1)$th sample falls on the same point of the E(t) waveform as the first sample. Thus, sample 70(d) is taken at exactly the same point of the E(t) waveform as sample 70(a). Stated another way, on each sample the sample is delayed relative to the E(t) waveform by $T_e/N_p$, so that after $N_p$ samples have been taken, the accumulated delay of the sample relative to the waveform is equal to $T_e$, i.e., one full repetition period of the waveform, and hence the next sample falls on the same point of the waveform as the first sample. Thus, the sampling is coherent with the excitation waveform. Every $N_p$ samples constitute a complete representation of a single cycle of the waveform. The sampling is continued over a sufficient time to accumulate many times $N_p$ samples.

While the samples are being acquired, computer 20 averages together all of the samples taken from a given point in the waveform. Thus, the computer averages the value recorded at sampling point 70(a), the value recorded at sampling point 70(d) and the value recorded at other sampling points (not shown) at the same point in the waveform, so as to derive an averaged value for all of the samples at this point in the waveform. In like fashion, computer 20 computes an average for all of the samples representing the second point in the waveform, i.e., for sample point 70(b), sample point 70(e) and other, similar values (not shown). Standard computer averaging techniques are used in this stage of the process. Thus, the individual samples are added into $N_p$ running totals maintained in $N_p$ separate memory registers. The computer directs every $(N_p+1)$th sample into the same memory register and the sample is added to the running total in that register. Each total is subsequently divided by the number of samples included in the total. $N_p$ separate averages are computed in this way. These $N_p$ averaged sample values constitute a sampled excitation signal, and collectively represent the complete waveform of the excitation signal E(t). Although the sampling period $T_s$ is actually longer than the repetition period $T_e$ of the waveform, the effective sampling rate is multiplied by a factor approximately equal to the absolute value of $N_w N_p$. Because the waveform is represented by $N_p$ sampled points, the effect is substantially the same as if the sampling rate were about $N_w N_p$ times as great, or as if the fundamental frequency of the excitation waveform E(t) were divided by about $N_w N_p$. This effect is indicated by the hypothetical E(t) sampled waveform depicted in broken lines in FIG. 3. Thus, the interval $T_s$ between successive samples is only a small fraction of the multiplied repetition period of the broken line waveform.

This effect can be explained in terms of sampling theory. Conventional and well-known sampling theory states that with ordinary, non wave-skipping sampling at a sampling rate $F_s$, the samples provide complete information as to the phase and modulation of components in the waveform up to a maximum frequency $F_h$ where $F_h = F_s/2$. With conventional sampling of a waveform having fundamental frequency $F_e$, $F_s = N_p F_e$ where $N_p$ is the number of samples per cycle of the waveform. Thus, for ordinary non wave-skipping sampling, $F_h = N_p F_e/2$. The same relationship between $F_h$, $N_p$ and $F_e$ applies to wave-skipping sampling. However, with wave-skipping sampling as described above, the relationship between $F_s$ and $F_e$ is different. For coherent wave-skipping sampling: $F_s = N_p F_e/(N_w N_p + 1)$. Thus, the relationship between the highest frequency for which information is provided by the samples and the sampling frequency is: $F_h = (N_w N_p + 1)F_s/2$. Stated another way, wave-skipping sampling multiplies the maximum frequency $F_h$ observable with a given sampling rate $F_s$ by a factor of about $N_w N_p$.

Conventional, readily available sampling and digitizing equipment such as conventional sample-and-hold circuits and analog to digital converters provide a maximum sampling frequency $F_s$ up to about 20 MHz. However, the value of $N_w N_p$ may be up to about several hundred or more. Thus, even with conventional sampling equipment, maximum values of $F_h$ up to several GHz can be obtained. Therefore, the samples can provide complete phase and modulation information for component frequencies from a few hertz to several GHz.

Specialized high rate sampling and digitizing equipment can provide even greater $F_s$ and correspondingly greater $F_h$. Although sampling devices are ordinarily not regarded as taking a point sample along a waveform, a real sampling device such as a sample-and-hold circuit actually provides a sample signal representing a portion of the waveform during some small but nonetheless finite sample capture interval. The wave-skipping technique does not appreciably enlarge the allowable sample capture interval. The sample capture interval used in wave-skipping sampling should be no more than the sample capture interval used with ordinary sampling, and desirably should be less than $T_e/N_p$.

To minimize aliasing, the harmonic content of the excitation signal desirably is limited to frequencies of about $F_h$ and below, by selecting the duty cycle of the excitation waveform such that the duty cycle $T_h/T_e$ is less than $1/N_p$.

After a predetermined number of samples have been taken with respect to the excitation waveform, computer 20 actuates optical switch 36 to direct the excitation light into the probe 42, thus starting a test cycle. During the test cycle, the excitation light is directed into the proximal end 44 of optical fiber 43, and passes through the optical fiber to the mass 48 of luminescent composition. While the repetitive bursts of excitation light are applied to the composition, the composition emits light in response to each burst of excitation light, and the intensity of each burst of emitted light decays after the end of a burst of excitation light. The repetitive bursts of emitted or response light are directed through the optical fiber 43 to the proximal end thereof and through switch 36 into detector 56. The emitted or response light impinging on detector 56 is converted by the detector and by amplification circuit 58 into an electrical response signal, which electrical signal passes through bandpass filter 60. At the beginning of the test cycle, aperture control unit 65 adjusts the aperture 32 so that the response light emitted by the luminescent composition in the probe will produce an electrical signal from amplifier 58 of the appropriate magnitude.

The electrical response signal passing to converter 62 from bandpass filter 60 is depicted schematically as F(t) in FIG. 3. This signal includes a repetitive series of decay periods. As each decay period corresponds to a single excitation light pulse, the response signal F(t) has the same fundamental frequency Fe and the same repetition period $T_e$ as the excitation signal E(t). Analog to digital converter 62 is operated in the same way as discussed above with reference to the excitation signal to take a series of samples of the response signal F(t), using the same sampling frequency $F_s$ and sampling period $T_s$. Here again, the sampling rate is coherent with the fundamental frequency of the waveform, in that the time $T_s$ between samples differs from the nearest integral multiple of the fundamental period $T_e$ of the waveform by a small amount $T_e/N_p$ where $N_p$ is a rational number having an absolute value greater than one. Therefore, after a finite number of fundamental periods or cycles of the waveform, the sample is taken at the same point of the F(t) waveform as previously taken. Most desirably, $N_p$ is an integer, so that after $N_p$ samples have been taken, the sampling point falls at the same point in the waveform as previously sampled. Thus, as indicated in FIG. 2, the sampling point 72(b) falls at the same point on the F(t) waveform as sampling point 72(a), taken $N_t$ samples previously. Here again, the effect is substantially the same as if the sampling rate were about $N_wN_p$ times higher or as if the frequency of the sampled F(t) were about $N_wN_p$ times lower, as indicated by the waveform F(t) sampled in FIG. 3.

The same increase in maximum observable frequency $F_h$ discussed above with reference to the excitation waveform E(t) also applies in sampling of the response signal F(t). As with the excitation samples, the response samples are captured and stored by memory access unit 64 in memory 22 in sequence, and plural samples representing the same point on the response waveform are averaged by computer 20 to provide an average value for each sampled point on the waveform.

Computer 20 actuates the other components of the apparatus to perform a plurality of reference and test cycles in the manner discussed above, in alternating sequence. The alternating test and reference cycles assure that any drift or variation in the properties of the instrument will be averaged out, and will have equal effects on the response and excitation signals. The data from each cycle (a series of averaged values) is maintained separate in memory 22. Once the required number of cycles has been completed, the computer applies a standard, well-known digital fast Fourier transform algorithm to the data. The individual sampled excitation and response signals constituted by each series of averaged values stored in memory 22 for each reference cycle and for each test cycle is separately transformed into a Fourier series expansion. The Fourier series expansion $(FS)_r$ of the response signal is given by the expression:

$$(FS)_r = \sum_{n=1}^{n=\frac{N_p}{2}} R_{n,r}\cos(2\pi n f_E t) + I_{n,r}\sin(2\pi n f_E t) \quad \text{(Formula II)}$$

where: $R_{n,r}$ is the real magnitude of the response signal component of the $n^{th}$ harmonic frequency and $I_{n,r}$ is the imaginary magnitude of the response component at the $n^{th}$ harmonic frequency. The Fourier series expansion $(FS)_e$ of the sampled excitation signal is given by an expression of the same format incorporating coefficients $R_{n,e}$ and $I_{n,e}$ representing the real and imaginary magnitudes, respectively, of the excitation signal component at the $n^{th}$ harmonic frequency. The phase delay or difference in phase between the response component at a given frequency and the excitation component at the same frequency is given by the expression:

$$\Delta\phi_w(n) = \arctan\left(\frac{I_{n,e}}{R_{n,e}}\right) - \arctan\left(\frac{I_{n,p}}{R_{n,p}}\right) \quad \text{(Formula III)}$$

where $\Delta\phi_\omega(\eta)$ is the phase delay for the $n^{th}$ harmonic.

The absolute modulation for each component in the Fourier series expansion of the sampled response signal is given by $$M_{n,p} = \frac{(R_{n,p}^2 + I_{n,p}^2)^{\frac{1}{2}}}{R_{0,p}} \quad \text{(Formula IV)}$$

where $R_{0,r}$ is the average intensity or D.C. level of the response signal. Likewise, the absolute modulation of each component in the excitation signal $M_{n,e}$ is given by the same expression but using the coefficients $R_{n,e}$, $I_{n,e}$ and $R_{0,e}$. Using these absolute modulations, the modulation ratio $M_n$ for the $n^{th}$ harmonic frequency is given by $$M_n = \frac{M_{n,r}}{M_{n,e}} \qquad \text{(Formula V)}$$

The modulation ratio for each component is a measure of the change in modulation at a given frequency.

The computation of each phase delay and of each modulation ratio $M_n$ involves comparison between characteristics of a characteristic of a given $n^{th}$ harmonic component in the Fourier series expansion of the sampled excitation waveform from one reference cycle with the corresponding characteristic of the component in the Fourier series expansion of the sampled response waveform from one test cycle. This comparison effectively removes instrumental effects. Both the excitation and response waveforms incorporate any distortion or phase delay and modulation caused by the instrument components. Once the phase delay and the modulation ratio have been computed separately for each test cycle, each of these parameters is averaged over all test cycles providing final average values for each parameter.

Because the Fourier series expansion incorporates waveform components at plural harmonics of the fundamental excitation frequency $F_e$, the instrument and the method discussed above effectively obtains information concerning the optical properties of the luminescent composition 44 at numerous frequencies in a single operation. Computer 20 may calculate luminescence decay parameters of the composition from these phase delays and modulation ratios. The computer may further translate the luminescence parameters of the composition into a value of bloodstream $PO_2$, based upon a predetermined calibration curve relating the luminescence parameters to $PO_2$.

The relationships employed to translate phase delays and modulation ratios at plural frequencies into an expression I(t) relating luminescent decay to time are known. Among the relationships which may be used are the following:

$$\tan(\Delta\phi_n) = \frac{S(nf_E)}{G(nf_E)} \qquad \text{(Formula VI)}$$

$$M_n = \frac{1}{N}[S^2(nf_E) + G^2(nf_E)]^{\frac{1}{2}} \qquad \text{(Formula VII)}$$

$$S(nf_E) = \int_0^\infty I(t)\sin(2\pi nf_E t)dt \qquad \text{(Formula VIII)}$$

$$G(nf_E) = \int_0^\infty I(t)\cos(2\pi nf_E t)dt \qquad \text{(Formula IX)}$$

$$N = \int_0^\infty I(t)dt \qquad \text{(Formula X)}$$

These relationships are applied by assuming a functional form for I(t) such as a simple experimental decay; a superposition of plural discrete or exponential decays; a superposition of continuous exponential decays in terms of lifetime distributions or probability density functions or a superposition of first and second order decays.

Determination of the decay characteristic I(t) from a frequency domain representation such as the Fourier series expansions discussed above provides a significantly enhanced resolution of short-time events in the decay. The time resolution for the frequency domain representation of a given sampled signal is substantially better than the time resolution which could be achieved by direct observation of the sampled signal itself. Stated another way, to measure an event having a given time span tau, such as a lifetime of an excited state contributing to a short lived luminescence such as fluorescence, a system employing a direct observation of the sampled waveform would require that times between samples be approximately equal to tau. However, when the frequency domain representation is observed the time between samples may be at least an order of magnitude greater than tau, and typically about 20(pi)(tau). In effect, the excitation and sampling rates may be relatively low when the frequency domain representation is employed.

In the system described above, both the wave-skipping sampling technique and the use of the frequency domain representation allow the instrument to detect very brief events having a small tau. Where the events to be measured are relatively slow, with a substantial value of tau, one of these approaches may be omitted. Thus, standard sampling techniques may be employed instead of the wave-skipping sampling techniques discussed above. The computer 20 simply sets $F_s$ such that $F_s = N_p F_e$, i.e., $N_w = 0$ in the expressions discussed above.

Figure 4:
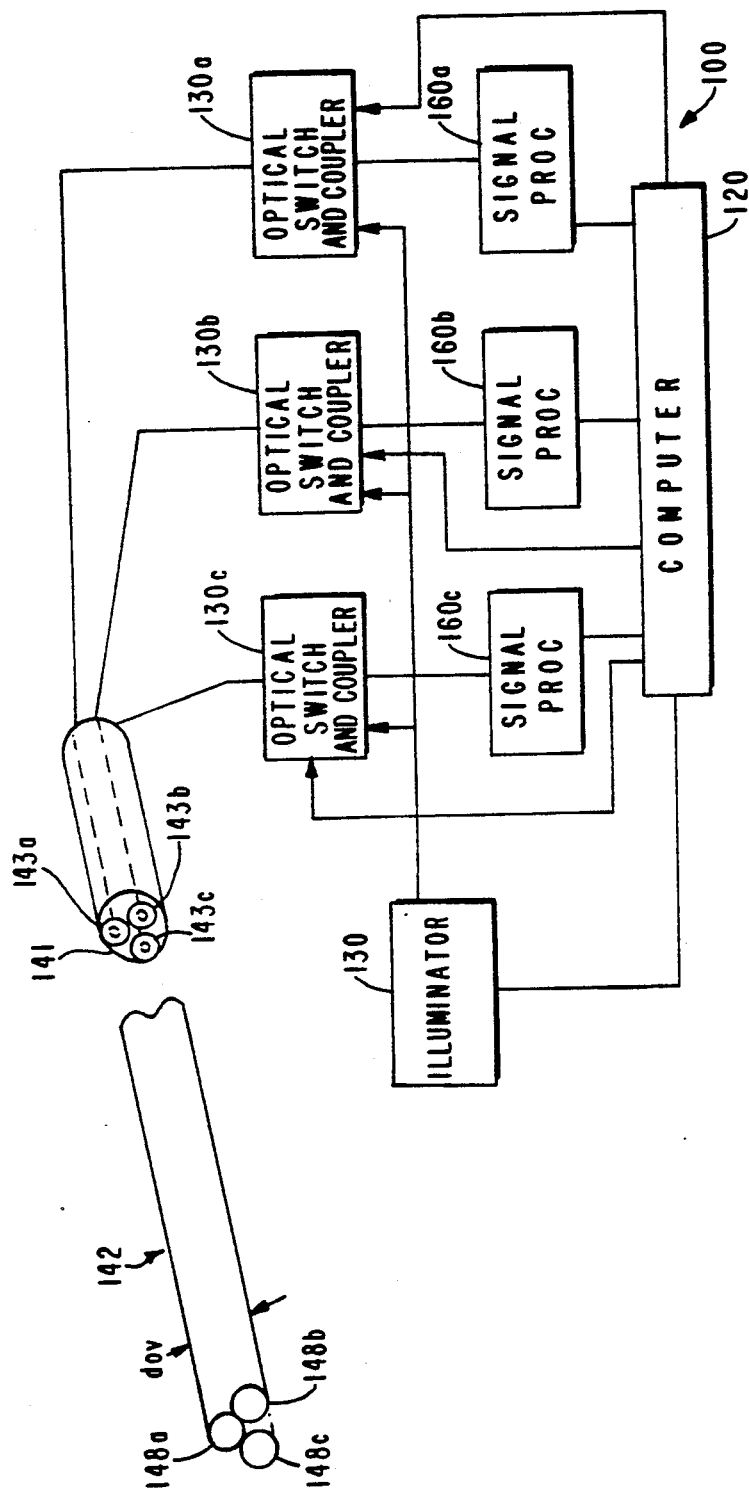
FIG. 4 is a further schematic, partially block diagrammatic view depicting apparatus according to another embodiment of the invention.

Apparatus in accordance with a further embodiment of the present invention is schematically illustrated in FIG. 4. This apparatus incorporates a composite probe 142. Probe 142 includes three optically transmissive fibers 143a, 143b, and 143c each of which is generally similar to the fiber optic 43 discussed above with reference to FIG. 1. The three fibers extend generally parallel to one another and are encased in a polymeric sheath 141 covering the fibers substantially from their proximal ends to their distal ends. The overall diameter $d_{ov}$ of the sheath desirably is less than about 450 micrometers. Therefore, the outside diameter of each fiber 143 desirably is about 140 micrometers. Fiber 143a has a mass 148a of a luminescent composition attached to the distal end of the fiber in light transmissive relation therewith, so that light passing from the proximal to the distal end of fiber 143a will be directed into mass 148a, whereas response light emitted by mass 148a will be directed along fiber 143a back towards the proximal end of such fiber. Fibers 143b and 143c have similar masses of luminescent material 148b and 148c attached to their respective distal ends, so that all of the masses of luminescent material 148 are disposed at the distal end of the composite probe. The masses of luminescent material are sensitive to different conditions. Thus, the luminescent material of mass 148a is an oxygen sensitive material similar to that discussed above. Mass 148a is composed of a luminescent material sensitive to pH whereas the composition of mass 148c is sensitive to carbon dioxide.

The pH sensitive composition of mass 148b may include a luminescent material which is sensitive to pH but substantially insensitive to oxygen. The luminescent material may be incorporated in a water-permeable polymer such as a methacrylate or an acrylamide. As used in this disclosure, the term "luminescent material" includes a combination of materials which cooperate to give the desired luminescent properties and/or sensitivity to the condition to be monitored. As disclosed in Jordan et al, Physiological pH Fiber-optic Chemical Sensor Based on Energy Transfer, Anal. Chem. 1987, vol. 59, pp. 437–439, a pH sensitive luminescent material may include a fluorophore such as eosine and an absorber such as phenol red co-immobilized or bound in a methacrylamide polymer. In such a system, the fluorophore itself may be a insensitive to the condition to be monitored such as pH but the absorber may be sensitive. In such a system, the absorber may absorb energy from the fluorophore, and thus diminish the net response or emission light, by directly absorbing response light emitted by the fluorophore or by non-radiative energy transfer from the fluorophore to the absorber so that the absorber serves to quench the fluorescence of the fluorphor. Both phenomenon may occur in the same luminescent composition. As the characteristics of the absorber change in response to the condition to be monitored, the degree of such absorption and/or quenching also changes, and hence the response of the luminescent material changes. Where the absorber provides quenching, the decay time characteristics of the response light will vary with the characteristics of the absorber. Other composite luminescent materials include an absorber adapted to absorb the excitation light. The carbon dioxide sensitive composition of mass 148c may incorporate a pH sensitive luminescent material and water permeable polymer similar to those employed in mass 148b, together with a bicarbonate and water buffer. Mass 148c may include a coating of a water impermeable, ion-permeable material to prevent drying of the buffer during storage.

Composite probe 142 is inserted into the body of a living organism in much the same fashion as probe 43 discussed above, so that all of the masses 148a, 148b and 148c of the various luminescent compositions are exposed to conditions prevailing within the body.

The apparatus also includes a multichannel illumination and signal processing apparatus 100 which includes three optical switches and couplers 136. Each of these optical switches is connected via conventional optical interconnection devices to the proximal end of one fiber 143. Apparatus 100 also includes an illumination device 30 which may incorporate a pulse generator, light pulse source and band pass optical filter similar to the corresponding components discussed above with reference to FIG. 1. Also, the apparatus incorporates three signal processing paths 160, each of which incorporates a detector, amplifier, band pass filter, analog to digital convertor and direct memory access unit similar to the corresponding components of FIG. 1. The apparatus further includes a computer 120 and associated clock, memory and data input and output components. Computer 120 is arranged to actuate the three optical switches 136a, 136b, and 136c in alternating sequence so as to link illuminator 130 alternately to each of the fibers 143a, 143b, and 143c and thus alternately select each fiber and the associated mass 148. While the illuminator 130 is linked to each fiber, computer 120 actuates the illuminator and the selected optical switch and coupler 136 and signal processing channel 160 to perform a sequence of operations similar to that described above. Thus, the components are activated to direct cyclically varying excitation light to the selected mass 148, to direct response light from the selected mass into the detector of the associated signal processing channel and to acquire a series of response sample values representing the luminescence of that particular mass. Each such series of response sample values is transformed into a frequency domain representation of the luminescent response, and the decay time parameters of the lumines-cence are derived from the characteristics of that frequency domain representation. The computer also actuates the selected optical switch and coupler to direct light from illuminator into the associated signal processing channel 160 for derivation of an excitation series of sample values representing the excitation light. These are processed as discussed above to yield a frequency domain representation of the excitation light for use as a reference standard in determining the luminescent decay time parameters of the selected composition. Computer 120 separately derives the luminescent decay time parameters of the luminescent material in each mass 148a, 148b, and 148c and translates these parameters into values for oxygen concentration, pH and carbon dioxide concentration or $PCO_2$ within the body of the subject.

The ability of the instrument to operate with fibers of relatively small diameter is particularly important in embodiments such as that of FIG. 4 employing a composite, multifiber probe. Because the outside diameter of each fiber 143 is relatively small, the probe as a whole including sheath 141, may have an overall diameter and maximum dimension transverse to its direction of elongation small enough to facilitate insertion of the probe into the body of a subject, as through an intravascular catheter or needle. Desirably, the overall diameter of the sheath 141 is about 450 microns or less. To provide such a small overall diameter, each fiber within the composite probe desirably has an outside diameter of about 140 microns or less. The masses 148 are arranged so that the maximum dimension across the masses in the direction transverse to the axis of elongation of fibers 143 is about 450 microns or less.

It is not essential to employ separate optical couplers and separate signal processing channels as discussed above in sensing multiple conditions within a subject using a single probe. A single optical coupler may be arranged to couple the various fibers of the probe in alternating sequence to a single processing channel, and the computer may be arranged to interpret the data derived from that signal channel as representing the luminescent response of the various compositions. Where the different luminescent materials exhibit changes in decay times on different time scales, the response of each composition to changes in the associated environmental condition will be incorporated in response components at markedly different frequencies. For example, where one material has a luminescent decay time in the pico second range which is affected by the environmental condition to be detected by that composition, and another material has a luminescent decay time in the millisecond range affected by its associated environmental condition, the response of the two materials may be monitored by a common detector and the components at these widely differing frequencies may be separated by appropriate band pass electrical filtering of the signal from the detector. In such an arrangement, excitation light incorporating components varying in amplitude at widely differing frequencies would be applied to both materials simultaneously. For example, the excitation light may include pulses at a relatively low first fundamental frequency together with harmonics of that low first fundamental, and the excitation light may also include pulses at a far higher second fundamental or pulse frequency together with harmonics of that second frequency. The sampling and subsequent processing steps may be conducted separately with respect to the separate signals in the different frequency bands. The plural luminescent materials in such an arrangement can be incorporated in one composition or in plural compositions.

In a variant of the multi-fiber, multi-mass apparatus described above with reference FIG. 4, one or more of the fibers may be connected to conventional luminescence intensity sensitive detection apparatus whereas one or more of the other fibers may be connected to luminescence time decay sensitive apparatus as described above. Such an approach may be used where the luminescence time decays of the luminescence material used for one or more of the masses 148 make it difficult or expensive to sense luminescence time decay characteristics. In this case, the luminescence time decay sensing according to the present invention will nonetheless provide benefits with respect to at least one of the luminescence signals from at least one of the compositions.

Numerous additional various and combinations of the features discussed above may be utilized in accordance with the broad compass of the present invention. As used in this disclosure, the word "light" includes not only visible light but also includes electromagnetic radiation beyond the visible spectrum, such as infrared and ultraviolet radiation. Thus, infrared and/or ultraviolet radiation may be incorporated in the excitation light or in the response light emitted by the luminescent composition. Further, conditions other that the specific chemical conditions discussed above may be monitored, provided that a luminescent material sensitive to the particular conditions is employed. Luminescent materials which are sensitive to conditions such as temperature and to chemical conditions other than $PO_2$, pH and $PCO_2$ are known to those skilled in the art, and any of these luminescent compositions may be employed provided that their luminescent time decay parameters vary repeatably with the conditions prevailing in the environment. Also, the instruments discussed above sample the excitation light to derive a reference for use in determination of luminescent time decay parameters. However, such sampling of the excitation light may be omitted and the luminescent time decay parameters may be derived from the frequency domain representation of the response signal based upon a known or assumed fixed standard.

In the apparatus discussed above, the detector produces a continuous electrical signal representing the light incident upon it, and this: signal is sampled discontinuously by one or more analog to digital converters. In an alternate arrangement, the detector may be operated discontinuously, as by triggering the detector response to the sampling trigger signal used to trigger the analog to digital converter in the embodiment discussed above. Triggerable detectors such as triggerable photomultiplier tubes are known in the art. Further, the particular light pulse source employed may incorporate substantially any effective light pulse source such as light emitting diodes or a continuous wave light source in conjunction with pulsing devices such as Pockel's cells or acousto-optical modulators.

In a variant of the wave-skipping sampling discussed above with reference to FIG. 3, the sampling may be performed asynchronously with respect to the excitation or reference signal being sampled, but nonetheless at a sampling frequency lower than the excitation frequency. In this variant, the sampling frequency and sampling period do not conform to the preferred relationship set forth in Formula I, above. Because the sampling frequency is lower than the excitation frequency, successive samples will be taken from different cycles of the waveform. As the sampling frequency differs from the fundamental frequency of the waveform, different samples will be taken at different phases of the waveform, just as in the coherent wave-skipping variant discussed above. In the asynchronous system, however, the samples do not fall on the same phase of the waveform after any predetermined number of samples have been taken. Thus, a large number of individual samples, each at a unique phase of the waveform can be collected. This set of unique samples may be processed to provide data essentially equivalent to the data from plural sets of repetition samples discussed above. Although plural unique sample values cannot be directly averaged, the sample values can be processed according to known mathematical techniques to provide a data-smoothing effect similar to averaging. Thus, known linear interpolation or autocorrelation techniques can be used to derive quasi-averaged amplitude values for each phase of the waveform from plural amplitude values in samples taken at neighboring phases.

As these and other various and combinations of the features described above may be employed, the foregoing description of preferred embodiment should be taken as illustrating, rather than as limiting, the invention as defined by the claims. The following nonlimiting example illustrates certain features of the invention.

EXAMPLE

An anesthetized dog is subjected to intraarterial oxygen partial pressure measurements over a period of ten hours using instruments and methods substantially as described above with reference to FIG. 1. Two separate probes are employed. Each probe incorporates a mass of platinum tetra (paraamino phenyl) porphine dispersed in a resin. In one case, the resin is commercially available polycarbonatepolydimethylsiloxane copolymer. In the other case, the resin is a silicone rubber. Each probe includes a quartz optical fiber having a core diameter of 100 micrometers and an outside or cladding diameter of 140 micrometers, the luminescent composition being bonded to the distal end of the fiber in each probe. Each probe is inserted into the femoral artery of the dog. Each probe is excited with pulsatile light at a fundamental excitation frequency or pulse frequency $F_e$ of 3.125 kHz, and the resulting response light from each probe is sampled at a sampling frequency $F_s$ of 50 kilo-Hertz utilizing an eight bit analog to digital converter. The response light produced by phosphorescence of the luminescent composition has an intensity or signal level of about 2.2 picowatts. The data is averaged 10,000 times in the time domain to yield an averaged response series of sample values, which is then transformed into a frequency domain representation of the response light signal. The sampling, averaging and transformation steps are repeated so as to yield a second frequency domain representation of the response light signal, and the characteristics of the first and second frequency domain representation are averaged with one another to yield a final, averaged, frequency domain representation. The characteristics of the final, averaged frequency domain representation are then used to derive a phosphorescence lifetime based upon an assumption of linear single exponential decay of the phosphorescent signal. This lifetime is then transformed to a value of oxygen partial pressure by using a Stern-Vollmer calibration function. The entire cycle, including sampling, averaging, first and second frequency domain transformations, lifetime determination and translation to oxygen partial pressure value consumes a test time of about seven seconds, and the cycle is repeated substantially continuously during the 10 hour test. Intrarterial blood samples are drawn periodically during the test and analyzed using a standard Nova Biomedical blood gas analyzer. The results obtained are illustrated in FIG. 5. The solid lines represent the results based upon the data from the two probes in accordance with the invention, whereas the small squares indicate control data taken using the aforementioned Nova Biomedical analyzer. The results show excellent agreement between the results from the two probes and also excellent agreement with the standard instrument.

We claim:

1. Apparatus for monitoring conditions within a living subject comprising:
    (a) a probe adapted for insertion into the body of a subject, said probe including an elongated optically transmissive fiber having a proximal end and a distal end, said probe also including a luminescent composition mounted at said distal end of said fiber in optical communication therewith, said luminescent composition having one or more luminescent decay time parameters affected by said condition when said distal end of said probe is disposed within the body of a subject;
    (b) means for applying to said composition through said fiber excitation light varying cyclically in amplitude, said excitation light incorporating components varying in amplitude at a plurality of excitation modulation frequencies simultaneously, whereby said luminescent composition will emit response light varying cyclically in amplitude and including a plurality of response components varying in amplitude at a plurality of response modulation frequencies simultaneously and said response light will be transmitted through said fiber to said proximal end thereof;
    (c) means for detecting the cyclically varying amplitude of said response light transmitted to said proximal end of said fiber and deriving a frequency domain representation of said cyclically varying response light amplitude including at least one characteristic of each of said plurality of response components; and
    (d) means for deriving values of one or more luminescence decay parameters of said composition from said characteristics, whereby said derived luminescence delay parameters will vary with said conditions.

2. Apparatus as claimed in claim 1 wherein said luminescence composition has one or more rapidly decaying luminescence modes having decay time less than about 100 nanoseconds and wherein said means for detecting said cyclically varying response light amplitude and deriving a frequency domain representation include means for deriving a frequency domain representation of components in said response light representing said one or more rapidly decaying luminescence modes.

3. Apparatus as claimed in claim 1 wherein said means for detecting said cyclically varying response light amplitude and deriving a frequency domain representation include means for directly sampling the amplitude of said response light and providing a response series of digital sample values each representing the amplitude of said response light at a predetermined point in the repetitive response light cycle, and a means for transforming said response series of digital sample values into said frequency domain representation.

4. Apparatus as claimed in claim 3 wherein said means for transforming includes means for applying a digital Fourier transform to said response series of sample values.

5. Apparatus as claimed in claim 3 wherein said means for sampling the amplitude of said light includes means for sampling said response light over a plurality of cycles of said response light to provide raw sample values from said plural cycles and means for averaging raw sample values from a plurality of cycles to provide each value in said response series of sample values.

6. Apparatus as claimed in claim 3 wherein said means for providing said response series of sample values includes means for providing a plurality of said response series of sample values and said means for transforming includes means for applying a transformation independently to each said response series of sample values to thereby provide a plurality of frequency domain representations of said response light each including said at least one characteristic of each of said plurality of response components, said means for deriving a frequency domain representation further comprising means for averaging values of each said characteristic in a plurality of said independent frequency domain representations to derive an averaged frequency domain representation, said means for deriving luminescent decay parameters from said characteristics including means for deriving said luminescent decay parameters from said characteristics in said averaged frequency domain representation.

7. Apparatus as claimed in claim 3 wherein said means for sampling said response light includes means for sampling said response light at a frequency lower than the lowest one of said excitation modulation frequencies.

8. Apparatus as claimed in claim 1 wherein said means for deriving a frequency domain representation includes means for deriving a phase angle for each said response component, and said means for deriving one or more luminescence decay parameters includes means for deriving said parameters at least in part from said phase angles.

9. Apparatus as claimed in claim 8 wherein said means for deriving one or more luminescence decay parameters includes means for deriving one or more decay exponents from said phase angles.

10. Apparatus as claimed in claim 1 wherein said means for deriving a frequency domain representation includes means for deriving a modulation value for each said response component, and said means for deriving one or more luminescence decay parameters includes means for deriving said parameters at least in part from said modulation values.

11. Apparatus as claimed in claim 1 wherein said fiber has a diameter less than about 450 micrometers.

12. Apparatus as claimed in claim 11 wherein said probe includes a plurality of fibers and said probe has an overall diameter less than about 450 micrometers.

13. Apparatus as claimed in claim 11 wherein said luminescent composition is disposed in a mass abutting the distal end of said fiber and wherein said mass has a maximum dimension in the direction transverse to the direction of elongation of said fiber less than about 450 micrometers.

14. Apparatus as claimed in claim 1 wherein said luminescent composition includes a luminescent material dispersed in a polymer.

15. Apparatus as claimed in claim 14 wherein said luminescent material is sensitive to oxygen and wherein said polymer is selected from the group consisting polyurethanes, polysiloxanes, polysiloxanepolycarbonate copolymers and combinations thereof.

16. Apparatus as claimed in claim 14 wherein said luminescent material is a compound selected from the group consisting of porphyrin; chlorin, bacteriochlorin, phosphorinogen and derivatives and combinations thereof.

17. A method of monitoring conditions within a living subject comprising the steps of:
   (a) inserting a probe including an elongated optically transmissive fiber and a luminescent composition mounted at a distal end of the fiber in optical communication therewith, into the body of the subject so that the distal end of the fiber is disposed within the body and one or more luminescent decay time parameters of the composition are affected by the condition to be monitored, and so that a proximal end of the fiber is disposed outside of the body;
   (b) directing excitation light through said fiber to said composition, said excitation light varying cyclically in amplitude, and incorporating components varying in amplitude at a plurality of excitation modulation frequencies simultaneously, whereby said luminescent composition will emit response light varying cyclically and including a plurality of response components varying in amplitude at a plurality of response modulation frequencies simultaneously and said response light will be transmitted through said fiber to said proximal end thereof;
   (c) detecting the cyclically varying amplitude of said response light transmitted to said proximal end of said fiber;
   (d) deriving a frequency domain representation of said cyclically varying response light amplitude including at least one characteristic of each of said plurality of response components; and
   (e) deriving a value of one or more luminescence decay parameters of said composition from said characteristics, whereby said derived luminescence delay parameters will vary with said conditions.

18. A method as claimed in claim 17 further comprising the step of translating said one or more derived luminescence decay parameters into a value of the condition to be monitored.

19. A method as claimed in claim 17 wherein one or more luminescence decay parameters include a decay time less than about 100 monoseconds.

20. A method as claimed in claim 17 wherein said step of detecting the cyclically varying amplitude of said response light and deriving a frequency domain representation includes the step of sampling the amplitude of said response light and providing a response series of sample values in digital form so that each said response light at a predetermined point in the repetitive response light cycle, and transforming said response series of sample values into said frequency domain representation.

21. A method as claimed in claim 20 wherein said step of transforming includes the step of applying a digital Fourier transform to said response series of sample values.

22. A method as claimed in claim 20 wherein said step of sampling the amplitude of said response light includes steps of sampling the response light over a plurality of cycles of said response light to provide raw sample values from said plural cycles and averaging raw sample values from a plurality of cycles to provide each value in said response series of sample values.

23. A method as claimed in claim 20 wherein said step of providing said response series of sample values includes the step of sampling the amplitude of said response light repeatedly to provide a plurality of said response series of sample values and said transforming step includes the step of applying a transformation independently to each said response series of sample values to thereby provide a plurality of frequency domain representations of said response light, each such representation including said at least one characteristic of each of said plurality of response components, said step of deriving a frequency domain representation further including the step of averaging values of each said characteristic in a plurality of said independent frequency domain representations to derive an average frequency domain representation, said step of deriving luminescent decay parameters from said characteristics including the step of deriving said luminescent decay parameters from said characteristics in said averaged frequency domain representation.

24. A method as claimed in claim 20 wherein said step of applying excitation light includes the step of applying said excitation light as a series of pulses at a fundamental frequency whereby said response light will include components varying in amplitude at said fundamental frequency and at harmonics thereof, and wherein said step of sampling the amplitude of said response light includes the step of sampling the amplitude of said response light at a sampling frequency lower than said fundamental frequency.

25. A method as claimed in claim 20 wherein said step of deriving a frequency domain representation includes the step of deriving a phase angle for each said response component, and said step of deriving one or more luminescence decay parameters includes the step of deriving said parameters at least in part from said phase angles.

26. A method as claimed in claim 20 wherein said step of the deriving a frequency domain representation includes the step of deriving a modulation value for each said response component, and wherein said step of deriving one or more luminescence decay parameters includes the step of deriving said parameters at least in part from said modulation values.

27. A method as claimed in claim 17 wherein said condition is the $PO_2$ of the blood in a mammal.

28. A method as claimed in claim 17 wherein said condition is the pH of the blood in a mammal.

29. A method as claimed in claim 17 wherein said condition is the $PCO_2$ of the blood in a mammal.

30. A method as claimed in claim 17 wherein said probe includes a plurality of optically transmissive fibers each having a luminescent composition mounted at the digital end thereof, each said luminescent composition being sensitive to a different condition to be sensed, said step of inserting said probe including the step of positioning all of said luminescent compositions within said subject, said step of directing excitation light, and response light including the steps of directing excitation light along each of said fibers, said step of detecting the cyclically varying amplitude of said response light including the step of detecting the amplitude of response light transmitted to the proximal end of each fiber, said step of deriving a frequency domain representation including the step of deriving a frequency domain representation of the response light amplitude from at least one of said fibers.

* * * * *